United States Patent [19]

Herrmann et al.

[11] Patent Number: 5,200,380
[45] Date of Patent: Apr. 6, 1993

[54] PROCESS FOR PRODUCING ALDEHYDES

[75] Inventors: Wolfgang Herrmann, Freising; Christian Kohlpaintner, Stephanskirchen; Helmut Bahrmann, Hamminkeln, all of Fed. Rep. of Germany

[73] Assignee: Hoechst Aktiengesellschaft, Fed. Rep. of Germany

[21] Appl. No.: 804,832

[22] Filed: Dec. 6, 1991

[30] Foreign Application Priority Data

Dec. 17, 1990 [DE] Fed. Rep. of Germany ....... 4040315

[51] Int. Cl.$^5$ ............... B01J 31/00; C07F 15/00; C07C 45/00
[52] U.S. Cl. .................... 502/166; 556/21; 556/136; 568/454; 502/168
[58] Field of Search ............... 556/21, 136; 568/454; 502/166, 168

[56] References Cited

U.S. PATENT DOCUMENTS

| 4,654,176 | 3/1987 | Dang et al. | 260/505 R |
|---|---|---|---|
| 4,694,109 | 9/1987 | Devon et al. | 568/454 |
| 4,742,178 | 5/1988 | Nelson et al. | 568/454 |
| 4,755,624 | 7/1988 | Phillips et al. | 568/454 |
| 4,760,194 | 7/1988 | Phillips et al. | 568/454 |
| 4,879,416 | 11/1989 | Puckette et al. | 568/13 |
| 4,904,808 | 2/1990 | Devon et al. | 556/21 |
| 4,994,427 | 2/1991 | Davis et al. | 502/166 |

FOREIGN PATENT DOCUMENTS

| 133127 | 2/1985 | European Pat. Off. |
| 279018 | 8/1988 | European Pat. Off. |
| 375573 | 6/1990 | European Pat. Off. |

Primary Examiner—José G. Dees
Assistant Examiner—Porfirio Nazario
Attorney, Agent, or Firm—Jordan B. Bierman

[57] ABSTRACT

The hydroformylation of olefins and olefinically unsaturated compounds in the presence of a water-soluble rhodium complex compound which contains, as a ligand, at least one sulfonated diphosphine, and a catalyst therefor.

2 Claims, No Drawings

PROCESS FOR PRODUCING ALDEHYDES

This Application claims the priority of German Application P 40 40 315.7, filed Dec. 17, 1990.

The present invention relates to a process for producing aldehydes by hydroformylation of olefins in the presence of water-soluble rhodium complex catalysts.

BACKGROUND OF THE INVENTION

It is known to produce aldehydes and alcohols, which contain one carbon atom more than the starting olefin, by reacting olefins with carbon monoxide and hydrogen (hydroformylation). The reaction is catalyzed by hydrido-metal carbonyls, preferably those of the metals of Group VIII of the Periodic Table (IUPAC Version). Apart from cobalt, which is widely used industrially as a catalyst metal, rhodium has recently been gaining increasing importance. In contrast to cobalt, rhodium allows the reaction to be carried out at a low pressure; furthermore, preferentially straight-chain n-aldehydes are formed, with an only minor fraction of iso-aldehydes. Finally, the hydrogenation of the olefins to give saturated hydrocarbons in the presence of rhodium catalysts is also markedly less extensive than with cobalt catalysts.

In the processes accepted in industry, the rhodium catalyst is employed in the form of modified hydridorhodium carbonyls which contain additional ligands, especially tertiary organic phosphines or phosphites. In most cases, there is an excess of the ligands, so that the catalyst system is composed of the complex compound and free ligand. The use of the rhodium catalysts described allows the hydroformylation reaction to be carried out at pressures below 30 MPa.

In this process, however, it is difficult to separate the reaction products and to recover the catalysts which are homogeneously dissolved in the reaction product. In general, the reaction product is distilled for this purpose out of the reaction mixture. In practice, however, because of the thermal sensitivity of the aldehydes and alcohols formed, this approach is feasible only in the hydroformylation of the lower olefins, i.e. olefins having up to about 8 carbon atoms in the molecule. In addition, it has been found that thermal stress on the distillation material also leads to considerable catalyst losses due to decomposition of the rhodium complex compounds.

The drawbacks described are avoided by the use of catalyst systems which are soluble in water. Such catalysts have been described, for example, in German Patent 26 27 354. The solubility of the rhodium complex compounds is achieved by the use of sulfonated triarylphosphines as a complexing constituent. In this process variant, the catalyst is separated from the reaction product after completion of the reaction, simply by separating the aqueous and organic phase; i.e. without distillation and hence without additional thermal process steps. A further feature of this procedure is that the n-aldehydes are formed with high selectivity from terminal olefins, with only very minor quantities of isoaldehyes. Sulfonated triarylphosphines and, in addition, carboxylated triarylphosphines are preferably used as complexing constituents of water-soluble rhodium complex compounds.

The known two-phase processes have proven to be highly suitable on an industrial scale. Nevertheless, efforts are being made to perfect the process even further. Thus, the prior art attempted to increase the activity of the catalysts by modification of the complex ligands and to extend their activity to further reduce the specific catalyst requirement—both rhodium and ligand—and hence the production costs. Economic factors are also the reason for working towards a marked reduction in the phosphine/rhodium ratio. A further improvement in the hitherto achieved high selectivity with respect to the formation of non-branched aldehydes is also desired. Several million tons of hydroformylation products are manufactured per year, so that even a small increase in the selectivity has economically significant consequences.

It is the object of the invention to improve the hydroformylation process as outlined above, i.e. to develop catalysts which exceed the activity and selectivity of known catalysts at a lower possible ligand/rhodium ratio.

SUMMARY OF THE INVENTION

The invention comprises a process for producing aldehydes by reacting monoolefins, unconjugated polyolefins, cycloolefins, or derivatives thereof with carbon monoxide and hydrogen at temperatures of 20° C. to 150° C. and pressures of 0.1 to 20 MPa. The reaction is carried out in the presence of water-soluble rhodium compounds, containing phosphines in complex bonding, as catalysts. The process comprises using, as the phosphines, biaryl derived diphosphines of Formula I

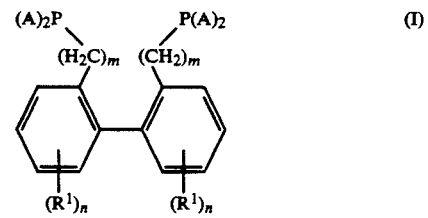

which are substituted by one or more sulfonic acid groups. The A radicals being independently alkyl, cycloalkyl, phenyl, tolyl, or naphthyl; the $R^1$ radicals being independently hydrogen, alkyl having 1 to 14 carbon atoms, alkoxy 1 having to 14 carbon atoms, cycloalkyl having 6 to 14 carbon atoms, aryl having 6 to 14 carbon atoms, aryloxy having 6 to 14 carbon atoms, or a fused benzene ring; the m's being independently integers from 0 to 5 and the n's being independently integers from 0 to 4.

The water-soluble rhodium/diphosphine complex compounds used as catalysts according to the novel process are distinguished by a remarkably high effectiveness, determined by the two criteria of "activity" A, namely $$A = \frac{\text{mole of aldehyde}}{\text{mol of Rh} \times \text{minute}}$$

and "productivity" P, namely $$P = \frac{\text{g of aldehyde}}{\text{ml of catalyst solution} \times \text{hour}}$$

The prior art values of these two parameters, are considerably exceeded by the procedure according to the invention. The formation of normal aldehydes increases further and the discharge of rare metal and phosphine with the reaction product is reduced. In addition, these results are achieved by the use of catalysts which have a markedly lower ligand/rhodium ratio than those used hitherto. These and other results, which are very valuable for carrying out the process on an industrial scale, were neither derivable from theoretical considerations nor foreseeable from experience in practice.

DETAILED DESCRIPTION OF THE INVENTION

The sulfonated diphosphines used as the catalyst constituent for the novel process can be prepared from biaryls, which are available by known syntheses, for example by coupling aryl-Grignard reagents with aryl halides. The introduction of the phosphorus-organic radical—$(H_2C)_mP(A)_2$—into the biaryl molecule is also carried out by conventional methods, for example by reacting a phosphorus compound of the general formula X—$(H_2C)_mP(A)_2$, in which X is a halogen atom, with the biaryl in the presence of a reagent which eliminates protons, such as sodium amide or butyllithium. In the last reaction step, the diphosphine is sulfonated with oleum, i.e. with a solution of sulfur trioxide in sulfuric acid, at temperatures of 0° C. to 60° C. The sulfonation product is isolated from the acidic solution, and diluted with water in accordance with the state of the art, for example by extraction with the solution of a water-insoluble amine in a water-insoluble organic solvent.

Preferred sulfonated diphosphines in the procedure according to the invention are those which are derived from biaryls of the general formula I, in which the A radicals are independently phenyl, tolyl, or naphthyl; the $R^1$ radicals are independently hydrogen, methyl, isopropyl, isobutyl, t-butyl, phenyl, naphthyl, or a fused benzene ring (so that a naphthyl structure is formed), m is 1, and n is 0 or 1.

Sulfonated diphosphines whose biaryl skeleton is substituted by radicals $R^1$ in the 6- and 6'-positions are also of great importance in the claimed process. The presence of these radicals hinders the rotation of the two substituted phenyl radicals. Rhodium complex compounds which contain such molecules as ligands can therefore be used as catalysts for enantioselective reactions.

Examples of diphosphines which are successfully used in the novel process are the products obtained by sulfonation of 2,2'-bis(diphenylphosphanomethyl)-biphenyl (hereinafter BISBIS) and of the 2-(diphenylphosphanomethyl)-1-[2-(diphenylphosphanomethyl)-phenyl]-naphthalene (hereinafter PHENAPS).

It is not necessary to use the disphosphines as single compounds. Mixtures of sulfonated disphosphines derived from biaryl compounds of different structure are also suitable as are mixtures of biaryls containing identical or different phosphine radicals and having different degrees of sulfonation. Finally, mixtures of sulfonated mono- and di-phosphines in combination with rhodium also give very active catalysts. Thus, for example, mixtures of BISBIS and Na triphenylphosphine-trisulfonate (called TPPTS below) have proven quite suitable.

It has also been found advantageous to use rhodium and sulfonated diphosphine not in the stoichiometric ratio, i.e. not corresponding to the chemical composition of the rhodium complex compound which forms in the course of the hydroformylation reaction, but to employ an excess of diphosphine. The rhodium/diphosphine ratio can here be varied within wide limits, and about 1 to 130 mol of diphosphine can be used per mol of rhodium. A rhodium/diphosphine molar ratio of 1:2 to 1:25 and especially 1:2 to 1:10 is preferred.

Rhodium is employed either as the metal or as a compound. In the metallic form, it is used either as finely dispersed particles or it is precipitated as a thin coating on a support such as activated carbon, calcium carbonate, aluminum silicate, or alumina. Suitable rhodium compounds are substances which are water-soluble or become water-soluble under the reaction conditions. The various rhodium oxides, salts of inorganic hydrogen acids, salts of oxygen acids, salts of aliphatic monocarboxylic acids, and salts of polycarboxylic acids are suitable. Examples of rhodium salts are rhodium nitrate, rhodium sulfate, rhodium acetate, rhodium 2-ethylhexanoate, and rhodium malonate. Rhodium halogen compounds are, however, less suitable because of the corrosive behavior of the halide ions. In addition, rhodium carbonyl compounds such as $Rh_3(CO)_{12}$, $Rh_6(CO)_{16}$, or complex salts of rhodium, e.g. cyclooctadienyl-rhodium compounds, can also be used. Rhodium oxide, and especially rhodium acetate and rhodium 2-ethylhexanoate are preferred. It must be assured that, in the presence of water gas, water-soluble rhodium complex compounds which contain carbon monoxide and diphosphine as ligands are formed under the conditions of the hydroformylation reaction. Together with the diphosphine dissolved in the water, they constitute the catalyst system.

The catalyst solution may be prepared from the components either in the hydroformylation reactor, or beforehand in separate equipment and then fed to the hydroformylation reactor. The concentration of rhodium in the aqueous catalyst solution is 20 to 1000 ppm by weight (based on the solution), preferably 100 to 600 ppm by weight, and most preferably 200 to 400 ppm by weight.

The reaction of the olefin with carbon monoxide and hydrogen takes place under pressures from about 0.1 to about 30 MPa, preferably about 1 to about 12 MPa, and most preferably about 3 to about 7 MPa. The composition of the synthesis gas, i.e. the volume ratio of carbon monoxide and hydrogen, can extend over wide ranges and be varied, for example, between 1:10 and 10:1. In general, gas mixtures are used in which the volume ratio of carbon monoxide and hydrogen is about 1:1 or deviates only slightly from this value in either direction. The reaction temperature is between about 20° C. and 150° C., preferably 80° C. to 140° C., and most preferably 100° C. to 125° C. are preferred.

The conversion of the reactants present in the liquid and gaseous phases takes place in conventional reactors. The progress of the reaction is decisively influenced by the fact that the aqueous catalyst solution must be saturated with the liquid or gaseous hydrophobic olefin and with the synthesis gas. It is therefore necessary to produce the greatest possible contact area between the phases. It has proven suitable to stir the liquid reactor contents (catalyst solution, if appropriate liquid olefin, and reaction product) intensively and to feed the gaseous reactants (synthesis gas and, if appropriate, olefin) to the liquid phase via distribution devices. It has been found to be very desirable to minimize the fraction of the organic phase in the reaction mixture. Surprisingly, the organic phase does not contribute to the solubility of the reactants in the aqueous phase, and undesired side reactions of the reaction product, which cannot be excluded in the case of increasing residence time of the product in the reactor, are avoided. Accordingly, the volume ratio of aqueous phase to organic phase is desirably 1:1 to 100:1, preferably 10:1 to 100:1. For this purpose, a corresponding part of the reaction mixture can be discharged continuously from the reactor, the aqueous and organic phases can be separated from one another and the aqueous phase can be recycled to the reactor. The reaction can be carried out batchwise or, preferably, continuously.

The process according to the invention is successfully applicable to the conversion of monoolefins, unconjugated polyolefins, cyclic olefins, and derivatives of these unsaturated compounds. The olefins can be straight- or branched chain, and the double bonds can be terminal or within the chain. Examples of olefins which can be used in the novel process are ethylene, propylene, butene-1, butene-2, pentene-1, 2-methyl-butene-1, hexene-1, hexene-2, heptene-1, octene-1, octene-3, 3-ethyl-hexene-1, decene-1, undecene-3, 4,4-dimethyl nonene-1, dicyclopentadiene, vinylcyclohexene, cyclooctadiene, and styrene. Examples of derivatives of the olefins which can be hydroformylated by the claimed procedure, are alcohols, aldehydes, carboxylic acids, esters, nitriles, and halogen compounds. Specifically, allyl alcohol, acrolein, methacrolein, crotonaldehyde, methyl acrylate, ethyl crotonate, diethyl fumarate, diethyl maleate, and acrylonitrile are advantageous. With particular success, the process is employed for the hydroformylation of olefins and olefin derivatives having 2 to 12 carbon atoms.

The examples which follow illustrate the invention, without restricting it to the embodiments described in detail.

EXAMPLES 1-4

A mixture of equal parts by volume of CO and H is fed into a 0.2 liter stainless steel autoclave fitted with a stirrer at a rate such that 10 liters (S.T.P.) of exit gas can be taken from the reactor per hour. At the same time, 300 ml of aqueous catalyst solution per hour are circulated through the reactor. The catalyst is composed of 0.09 g of rhodium (as the acetate) and 5.89 mmol of P(III) (in the form of BISBIS), which have been dissolved in degassed and nitrogen-saturated water to give 300 ml of solution. The phosphorus/rhodium molar ratio is 6.7:1, corresponding to a ligand/rhodium ratio of 3.4:1. The reaction of the reactants takes place at a temperature of 122° C. and a pressure of 5 MPa.

In the table 1 which follows, the results of the process according to the invention (Examples 1 to 3) are compared with Example 4 which is a procedure according to the state of the prior art (catalyst:rhodium/TPPTS). Examples 2 and 3 show very clearly that the novel procedure permits, in a completely surprising manner, a considerable increase in the propylene feed rate. Under such reaction conditions, the known processes with Rh/TPPTS catalysts give only very low conversions or none at all.

TABLE 1

| Experimental conditions | Example 1 | Example 2 | Example 3 | Example 4 (comparison) |
|---|---|---|---|---|
| Catalyst | Rh/BISBIS | Rh/BISBIS | Rh/BISBIS | Rh/TPPTS |
| Rhodium/ligand (mol/mol) | 1:3.4 | 1:3.4 | 1:3.4 | 1:80 |
| Temperature (°C.) | 122 | 123.5 | 122 | 122 |
| Pressure (MPa) | 5.0 | 5.0 | 5.0 | 5.0 |
| Propylene feed rate (g/h) | 39.0 | 91.6 | 110.6 | 37.6 |
| Experimental results | | | | |
| Conversion (%) | 79.9 | 57.8 | 47.9 | 41.8 |
| Activity $\frac{\text{mol (n + i) of aldehyde}}{\text{mol of Rh} \times \text{minute}}$ | 30.25 | 60.5 | 90.4 | 15.8 |
| Productivity $\frac{\text{g (n + i) of aldehyde}}{\text{ml of catalyst solution} \times \text{h}}$ | 0.412 | 0.824 | 1.16 | 0.213 |
| n-Aldehyde (g/h) | 49.2 | 98.2 | 90.8 | 28.0 |
| n/i ratio (parts by weight) | 97/3 | 97/3 | 96/4 | 94/6 |
| Alcohol (%) | 8.45 | 1.34 | 2.07 | 0.73 |
| Others (%) | 1.5 | 0.16 | 0.24 | 0.57 |

While only a limited number of specific embodiments have been expressly disclosed, it is, nonetheless, to be broadly construed, and not to be limited except by the character of the claims appended hereto.

EXAMPLES 5-14

Examples 5 to 14 relate to the hydroformylation of propylene in the apparatus used in the Examples 1 to 4. The reaction conditions are summarized below, the results of the experiments are summarized in Table 2.

| Reaction conditions | |
|---|---|
| Catalyst | Rh/BISBIS |
| Rh concentration (ppm, based on the catalyst solution) | 306 |
| Rh/ligand (mol/mol) | 1:3.4 |
| Temperature (°C.) | 125 |
| Pressure (MPa) | 5 |

TABLE 2

| | Examples | | | | | | | | | |
|---|---|---|---|---|---|---|---|---|---|---|
| | 5 | 6 | 7 | 8 | 9 | 10 | 11 | 12 | 13 | 14 |
| Propylene feed rate (g/h) | 23.0 | 49.9 | 65.9 | 82.7 | 100.8 | 110.6 | 128.4 | 125.2 | 124.0 | 108.0 |
| Activity $\frac{\text{mol (n + i) aldehyde}}{\text{mol Rh} \times \text{min}}$ | 27.45 | 42.4 | 54.58 | 67.37 | 64.37 | 90.47 | 90.31 | 46.29 | 31.04 | 97.68 |

TABLE 2-continued

| | Examples | | | | | | | | | |
|---|---|---|---|---|---|---|---|---|---|---|
| | 5 | 6 | 7 | 8 | 9 | 10 | 11 | 12 | 13 | 14 |
| Productivity $\frac{g (n + i) \text{ aldehyde}}{\text{ml of catalyst solution} \times h}$ | 0.35 | 0.55 | 0.70 | 0.87 | 0.83 | 1.16 | 1.16 | 0.60 | 0.40 | 1.26 |
| n-Aldehyde (g/h) | 83.48 | 84.59 | 85.46 | 87.58 | 89.73 | 87.64 | 88.0 | 89.35 | 89.00 | 87.37 |
| n/i ratio (parts by weight) | 95.61 | 97.05 | 96.12 | 95.81 | 95.89 | 95.72 | 92.26 | 96.45 | 96.51 | 96.86 |
| Alcohol (parts by weight) | 9.82 | 9.25 | 6.12 | 3.36 | 2.13 | 2.37 | 1.85 | 1.70 | 1.72 | 1.37 |

EXAMPLES 15-19

Examples 15 to 19 relate to the hydroformylation of hexene in the apparatus used in Examples 15 to 19. the reaction conditions are summarized below, the results of the experiments are summarized in Table 3.

| Reaction conditions | |
|---|---|
| Catalyst | Rh/BISBIS |
| Rh concentration (ppm, based on the catalyst solution) | 306 |
| Rh/ligand (mol/mol) | 1:3.4 |
| Pressure (MPa) | .5 |

TABLE 3

| | Examples | | | | |
|---|---|---|---|---|---|
| | 15 | 16 | 17 | 18 | 19 |
| Hexene feed rate (g/h) | 14.50 | 13.90 | 13.90 | 15.50 | 15.40 |
| Activity $\frac{\text{mol (n + i) aldehyde}}{\text{mol Rh} \times \text{min}}$ | 0.73 | 1.27 | 1.99 | 4.16 | 10.69 |
| Productivity $\frac{g (n + i) \text{ aldehyde}}{\text{ml of catalyst solution} \times h}$ | 0.004 | 0.007 | 0.011 | 0.023 | 0.058 |
| n-Aldehyde (g/h) | 4.60 | 8.90 | 13.80 | 26.10 | 30.30 |
| n/i ratio (parts by weight) | 97.12 | 96.23 | 96.00 | 95.38 | 94.56 |

What we claim is:

1. A catalyst for hydroformylation of a monomer selected from the group consisting of monoolefins, unconjugated polyolefins, cycloolefins, and derivatives thereof, said catalyst containing rhodium and a diphosphine, said diphosphine resulting from sulfonation of biaryl compounds of Formula I

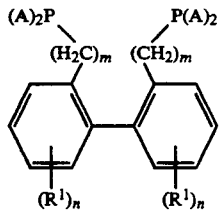

wherein the A radicals are independently alkyl, cycloalkyl, phenyl, tolyl, or naphthyl; the $R^1$ radicals are independently hydrogen, alkyl having 1 to 14 carbon atoms, alkoxy having 1 to 14 carbon atoms, aryloxy having 1 to 14 carbon atoms, cycloalkyl having 6 to 14 carbon atoms, aryl having 6 to 14 carbon atoms, aryloxy having 6 to 14 carbon atoms, or a fused benzene ring; the m's are independently integers from 0 to 5, and the n's are independently integers from 0 to 4.

2. The catalyst of claim 1 wherein said rhodium and said diphosphine are present in a molar ratio of 2:1 to 1:2.

* * * * *